US012583810B2

(12) United States Patent
Hunt et al.

(10) Patent No.: US 12,583,810 B2
(45) Date of Patent: Mar. 24, 2026

(54) TRICKLE BED REACTOR

(71) Applicant: Solugen, Inc., Houston, TX (US)

(72) Inventors: Sean Hunt, Houston, TX (US); Kevin Loftis, Bulverde, TX (US); Peter Nguyen, Saugus, CA (US); Parth Patel, Monmouth Junction, NJ (US)

(73) Assignee: SOLUGEN, INC., Houston, TX (US)

( * ) Notice: Subject to any disclaimer, the term of this patent is extended or adjusted under 35 U.S.C. 154(b) by 610 days.

(21) Appl. No.: 17/924,122

(22) PCT Filed: Jun. 1, 2021

(86) PCT No.: PCT/US2021/035235
§ 371 (c)(1),
(2) Date: Nov. 9, 2022

(87) PCT Pub. No.: WO2021/247563
PCT Pub. Date: Dec. 9, 2021

(65) Prior Publication Data
US 2023/0174448 A1 Jun. 8, 2023

Related U.S. Application Data

(60) Provisional application No. 63/032,780, filed on Jun. 1, 2020.

(51) Int. Cl.
B01J 8/04 (2006.01)
C07C 51/235 (2006.01)

(52) U.S. Cl.
CPC .............. C07C 51/235 (2013.01); B01J 8/04 (2013.01); B01J 8/0492 (2013.01); B01J 8/0496 (2013.01);
(Continued)

(58) Field of Classification Search
CPC ......... C07C 51/235; B01J 8/04; B01J 8/0496; B01J 8/0492
See application file for complete search history.

(56) References Cited

U.S. PATENT DOCUMENTS

| | | |
|---|---|---|
| 4,542,252 A | 9/1985 | Graziani et al. |
| 7,014,750 B2 | 3/2006 | Boger et al. |
| | (Continued) | |

FOREIGN PATENT DOCUMENTS

| | | |
|---|---|---|
| EP | 0794241 A2 | 9/1997 |
| JP | 2016-060712 A | 4/2016 |
| | (Continued) | |

OTHER PUBLICATIONS

PCT/US2021/035235 International Search Report and Written Opinion dated Aug. 31, 2021 (15p.).
(Continued)

*Primary Examiner* — Yate' K Cutliff
(74) *Attorney, Agent, or Firm* — CONLEY ROSE, P.C.

(57) ABSTRACT

A trickle bed reactor, comprising a plurality of catalyst beds connected in series and progressively increasing in catalyst mass in a direction from upstream to downstream; and a plurality of heat exchangers, wherein each of the heat exchangers is located between two of the plurality of catalyst beds, and wherein each of the heat exchangers does not exchange heat with an outer surface of a vessel that contains any of the catalyst beds.

20 Claims, 4 Drawing Sheets

(52) U.S. Cl.
CPC .......................... *B01J 2208/00168* (2013.01);
*B01J 2208/027* (2013.01)

(56) References Cited

U.S. PATENT DOCUMENTS

| | | | |
|---|---|---|---|
| 7,316,804 B2 | 1/2008 | Taheri et al. | |
| 7,692,041 B2 | 4/2010 | Kiely et al. | |
| 8,314,276 B2 | 11/2012 | Petri et al. | |
| 8,900,443 B2 | 12/2014 | Sechrist et al. | |
| 11,104,634 B2 * | 8/2021 | Vautravers | B01J 23/42 |
| 2003/0012711 A1 | 1/2003 | Harkins et al. | |
| 2012/0273391 A1 | 11/2012 | Dindi et al. | |
| 2014/0378700 A1 | 12/2014 | Majumder et al. | |
| 2015/0321974 A1 * | 11/2015 | Schammel | B01J 8/067 |
| | | | 422/198 |
| 2019/0185759 A1 * | 6/2019 | Kanervo | C10M 105/20 |

FOREIGN PATENT DOCUMENTS

| | | | | |
|---|---|---|---|---|
| JP | 2016060712 | * | 4/2016 | C07C 51/235 |
| JP | 2019-521126 A | | 7/2019 | |

OTHER PUBLICATIONS

Singapore Search Report and Written Opinion dated May 27, 2024 for Singapore Application No. 11202260471V (12 p.).

Mehtio, Tuomas et al., "Production and Applications of Carbohydrate-Derived Sugar Acids as Generic Biobased Chemicals," Critical Reviews in Biotechnology, vol. 36, No. 5, 2016, pp. 904-916 (14 p.)

Smith, Tyler N., "Sugar to Glucaric Acid: A Sweet Path to Renewable Chemicals," AOCS Inform Magazine, vol. 22, No. 9, pp. 550-552, 584 (4 p.)

"Johnson Matthey Davy Technologies and Rennovia to Develop and Commercialize Production Technology for Bio-Based Glucaric Acid & Adipic Acid" Mar. 20, 2014 (https://www.greencarcongress.com/2014/03/20140320-rennovia.html) (2 p.).

Solmi, Stefania et al., "The Oxidation of D-Glucose to Glucaric Acid Using Au/C Catalysts," ChemCatChem, The European Society Journal for Catalysis, vol. 9, No. 14, pp. 2797-2806, Mar. 9, 2017 (11 p.).

European Search Report dated Jul. 4, 2024 for European Application No. 21818235.0 (10 p.).

Japanese Office Action dated Apr. 22, 2025, for Japanese Application No. 2022-573710 (5 p.).

English Translation of Japanese Office Action dated Apr. 22, 2025, for Japanese Application No. 2022-573710 (6 p.).

Japanese Office Action dated Aug. 12, 2025 for Japanese Application No. 2022-573710 (3 p.).

English Translation of Japanese Office Action dated Aug. 12, 2025, for Japanese Application No. 2022-573710 (3 p.).

Indonesian Office Action dated Dec. 23, 2025, for Indonesian Application No. P00202213421 (3 p.).

English Translation of Indonesian Office Action dated Dec. 23, 2025, for Indonesian Application No. P00202213421 (3 p.).

Korean Office Action dated Nov. 17, 2025, for Korean Application No. 10-2022-7046282 (7 p.).

English Summary of Korean Office Action dated Nov. 17, 2025, for Korean Application No. 10-2022-7046282 (5 p.).

* cited by examiner

TRICKLE BED REACTOR

CROSS-REFERENCE TO RELATED APPLICATIONS

This application is a 35 U.S.C. § 371 national stage application of PCT/US2021/035235 filed Jun. 1, 2021, entitled "Trickle Bed Reactor," which claims benefit of U.S. provisional patent application Ser. No. 63/032,780 filed Jun. 1, 2020, and entitled "Trickle Bed Reactor," each of which is hereby incorporated herein by reference in its entirety for all purposes.

STATEMENT REGARDING FEDERALLY SPONSORED RESEARCH OR DEVELOPMENT

Not applicable.

FIELD

The present disclosure relates to trickle bed reactors.

BACKGROUND

Trickle bed reactors are solid-liquid-gas contacting devices in which a liquid stream flows downward over a bed of catalyst with a pressure differential serving as the driving force. The fluid flows over catalyst particles and forms fine films, rivulets, or droplets. The gas stream can either flow concurrent with the liquid or countercurrent to it through the bed. Trickle bed reactors are primarily operated in continuous mode but are sometimes used in semi-batch processes.

Trickle bed reactors (TBRs) are named as such for their operation in a trickle-flow regime. This regime is characterized by stable and continuous flow of the liquid and gas streams through the bed, similar to laminar flow in a single-phase system. The regime in which the system operates is dependent on the velocities of the liquid and gas streams. TBRs can also be run in pulsing, spray, or bubble flow regimes depending on the application.

Three-phase reactions are typically performed using either a TBR that operates as a Plug Flow Reactor (PFR) or a Slurry Reactor (SR) that can be designed either in a Continuous Stir Tank Reactor (CSTR) or PFR configuration. In general, TBRs can be the least expensive, most scalable, and most operationally robust of the well-known systems. Similarly, a PFR configuration can be better than a CSTR configuration, allowing for a high conversion with high selectivity and the smallest reactor working volume.

SUMMARY

Disclosed herein is a trickle bed reactor, comprising a plurality of catalyst beds connected in series and progressively increasing in catalyst mass in a direction from upstream to downstream; and a plurality of heat exchangers, wherein each of the heat exchangers is located between two of the plurality of catalyst beds, and wherein each of the heat exchangers does not exchange heat with an outer surface of a vessel that contains any of the catalyst beds.

Also disclosed herein is a method for operating a trickle bed reactor, the method comprising passing one or more reactants over a plurality of catalyst beds connected in series and progressively increasing in catalyst mass in a direction from upstream to downstream; wherein the trickle bed reactor comprises a plurality of heat exchangers, wherein each of the heat exchangers is located between two of the plurality of catalyst beds, and wherein each of the heat exchangers does not exchange heat with an outer surface of a vessel that contains any of the catalyst beds.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
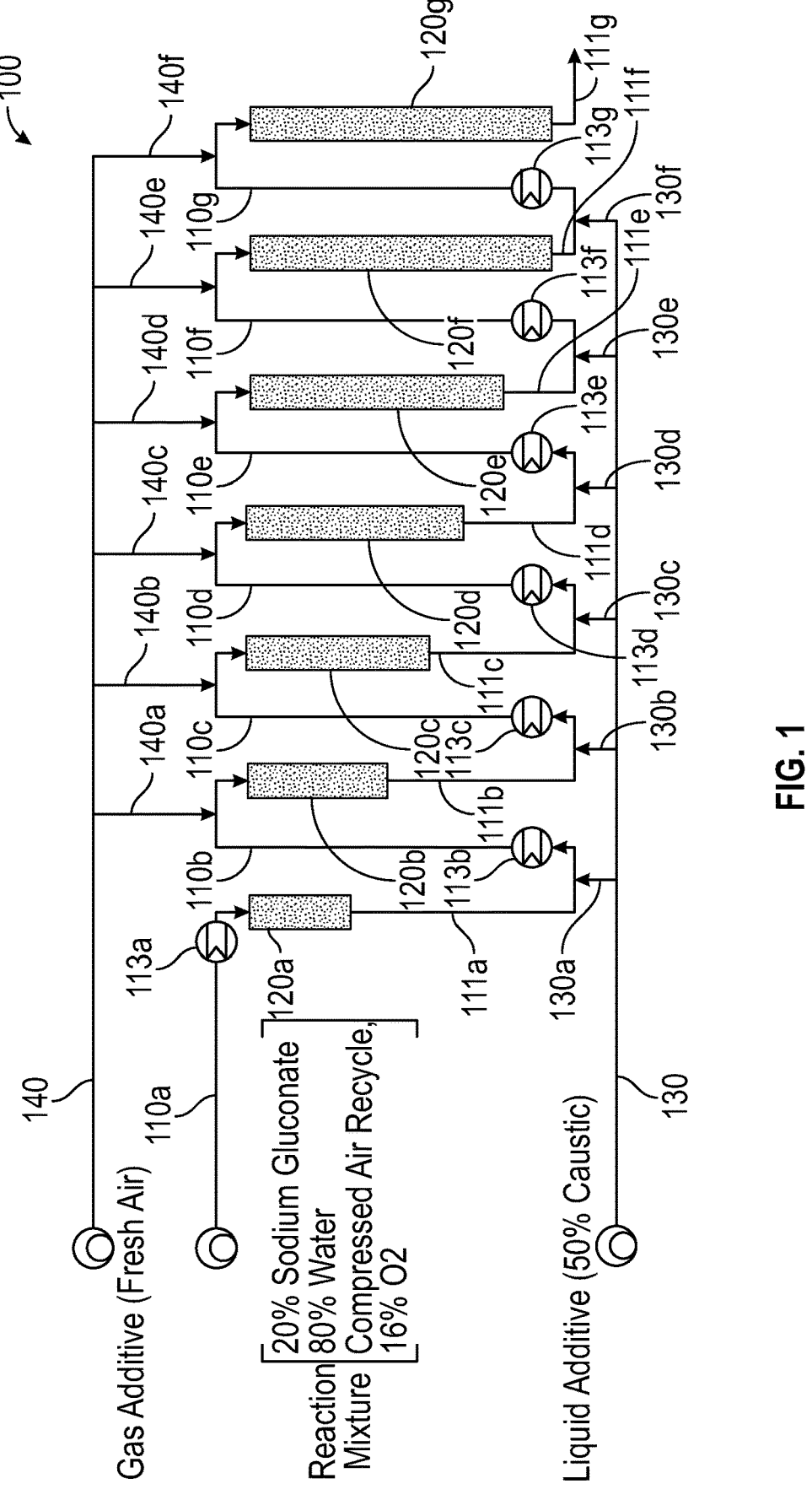
FIG. 1 is a schematic view of a reactor configuration in accordance with an aspect of the present disclosure.

A traditional fixed bed reactor for an exothermic three-phase reaction consists of dozens to hundreds of 1-2" diameter parallel tubes surrounded by a pressurized shell containing a heat transfer fluid. This configuration has expensive capital costs, is not robust for a three-phase reaction, and presents control challenges for three-phase reactions that exhibit a considerable exotherm or endotherm. Subtle differences in the solid packing density from tube to tube can create non-uniform distribution of the continuous gas and dispersed liquid flow rates through each parallel tube, especially as more and more tubes are added in parallel to scale up the reactor. This can create dead zones with low productivity catalyst and hot zones of high productivity catalyst. Poorly dispersed liquid flows can also have effects on selectivity and stability of the catalyst. Because each tube is surrounded by the shell containing the heat transfer fluid, it is not practical to inject gas or liquid into any of the tubes along the reaction coordinate, especially when there are dozens or hundreds of tubes. Shell-and-tube designs are also considerably more expensive from a total installed capital standpoint. Accordingly, there is an ongoing need for improved reactor configurations.

Aspects of apparatus and methods are disclosed herein that enable relatively low-cost trickle bed reactor configurations that operate in a trickle flow regime (e.g., gas continuous, liquid dispersed) to properly manage reaction exotherm or endotherm without the use of either parallel tubes filled with particulates and surrounded by a shell of heat transfer fluid. Such benefits can be achieved while accommodating reactions that include the continuous or periodic injection of gas additive and/or liquid additive at different locations in the reaction coordinate.

As used herein, the terms "line", "conduit", and "stream" interchangeably refer to the physical structure (e.g., piping) through which a gas, liquid, solid, or a combination thereof flows.

As used herein, the term "reaction coordinate" refers to the reaction path along which a reaction mixture travels in the disclosed apparatus and method. A point on the reaction coordinate may have a particular composition of the reaction mixture that is different from another point. For example, the beginning of the reaction coordinate contains 100% reactants, inert carrier materials, or both, and the end of the reaction coordinate can contain products, unreacted reactants, byproducts, inert carrier materials, or a combination thereof. In the alternative, the beginning of the reaction coordinate contains reactants, inert carrier materials, recycle products originating from a prior reaction or a combination thereof.

As used herein, the term "reaction mixture" refers to the components contained in the apparatus or method at a particular location in the apparatus or a particular point in the reaction coordinate. For example, the reaction mixture entering the apparatus or method contains 100% reactants, inert carrier materials, or both; and the reaction mixture leaving the apparatus or method contains products, unreacted reactants, byproducts, inert carrier materials, or a combination thereof.

FIG. 1 shows a process flow diagram of an aspect of a trickle bed apparatus 100. Reaction mixture can flow into the apparatus 100 via line 110a. Generally, the reaction mixture follows the flow path through lines 110a-g, 111a-g, and 112a-f, through catalyst beds 120a-g, and through heat exchangers 113a-g. That is, gas, liquid, and solid flow concurrently through the apparatus 100. For exothermic reactions, heat exchangers 113b-g are configured to cool the reaction mixture passing therethrough, and for endothermic reactions, heat exchangers 113b-g are configured to heat the reaction mixture passing therethrough. In some aspects, heat exchanger 113a is configured to adjust the temperature of the reaction mixture to initiate the reaction in the first catalyst bed 120a. For various reactions, this can include heating or cooling the reaction mixture to reaction temperature as desired for the process conditions at the inlet to the reactor. Liquid additive can flow in line 130, which splits into lines 130a-f so as to inject liquid additive into lines 111a-f, respectively. Gas additive can flow in line 140, which splits into lines 140a-f so as to inject gas additive into lines 110b-g, respectively. The rate of liquid and gas addition in these lines can be automated and controlled by various process measurements. Reaction mixture containing product, any unreacted reactants, any inert materials, and any byproducts can flow from the apparatus 100 in line 111g.

In FIG. 1, gas additive can be selectively injected via lines 140a-f into one or more lines 110b-g at locations that are between heat exchangers 113b-g and corresponding catalyst beds 120b-g. The amount of gas selectively injected via lines 140a-f can be the same in each line or selectively varied across each injection location to meet some user and/or process objective. Liquid additive can be selectively injected via one or more lines 130a-f into corresponding lines 111a-f at locations that are between catalyst beds 120a-g and corresponding heat exchangers 113b-g (e.g., upstream of the heat exchangers), for example, for an exothermic reaction. It is contemplated that liquid additive can alternatively be selectively injected via one or more lines 130a-f into lines 110b-g at locations that are between heat exchangers 113b-g and corresponding catalyst beds 120b-g (e.g., downstream of the heat exchangers), for example, for an endothermic reaction. The amount of liquid additive selectively injected via lines 130a-f can be the same in each line or selectively varied across each injection location to meet some user and/or process objective.

As can be seen in FIG. 1, there are seven catalyst beds 120a-g connected in series. The mass of catalyst in catalyst bed 120a is less than the mass of catalyst in catalyst bed 120b, which is less than the mass of catalyst in catalyst bed 120c, which is less than the mass of catalyst in catalyst bed 120d, which less than the mass of catalyst in catalyst bed 120e, which less than the mass of catalyst in catalyst bed 120f, which less than the mass of catalyst in catalyst bed 120g. Thus, the mass of the catalyst is successively increased in the catalyst beds 120a-g in the downstream direction. In general, the mass of the catalyst can be successively increased in the catalyst beds 120a-g in the downstream direction by any technique, such as by using a larger diameter vessel to contain the catalyst bed while maintaining the same length of catalyst bed (e.g., catalyst bed 120b has a larger diameter than catalyst bed 120a while having the same length), using a longer catalyst bed while maintaining the same diameter (e.g., catalyst bed 120b is longer than catalyst bed 120a while having the same diameter), decreasing the amount of inert solid materials mixed with a solid catalyst in catalyst beds all having the same dimensions in a downstream direction (e.g., catalyst bed 120a has 90 weight percent (wt. %) inert solid materials mixed with a solid catalyst and 10 wt. % catalyst, catalyst bed 120b has 80 wt. % inert solid materials mixed with a solid catalyst and 20 wt. % catalyst, and so on, while the catalyst beds 120a and 120b are the same size), or a combination thereof. Any other suitable techniques can also be used to provide an increasing mass of the catalyst in the downstream direction relative to the reaction mixture flow. In an aspect, the mass of catalyst in the catalyst beds differ by from about 1% to about 85%, alternatively from about 1% to about 70%, alternatively from about 75% to about 85% or alternatively about 85% based on the total weight of the catalyst. In one or more aspects, the catalyst mass increases by from about 100 kg to about 1,000,000 kg.

While FIG. 1 shows seven reactor vessels, it is contemplated that the catalyst beds 120a-g can be embodied as fixed catalyst beds contained in any number of reaction vessels, for example, 1, 2, 3, 4, 5, 6, 7, or more vessels.

Heat removal using a TBR of the type disclosed herein can be performed by heat exchangers 113a-g that are fluidly connected to the catalyst beds 120a-g. This mechanism of heat removal is in sharp contrast to a TBR configuration comprising a single shell containing heat transfer fluid that surrounds the vessels containing the catalyst. In some aspects, the catalyst beds 120a-g can be adiabatic reactor sections with heat exchange only occurring between the catalyst beds 120a-g.

Figure 2:
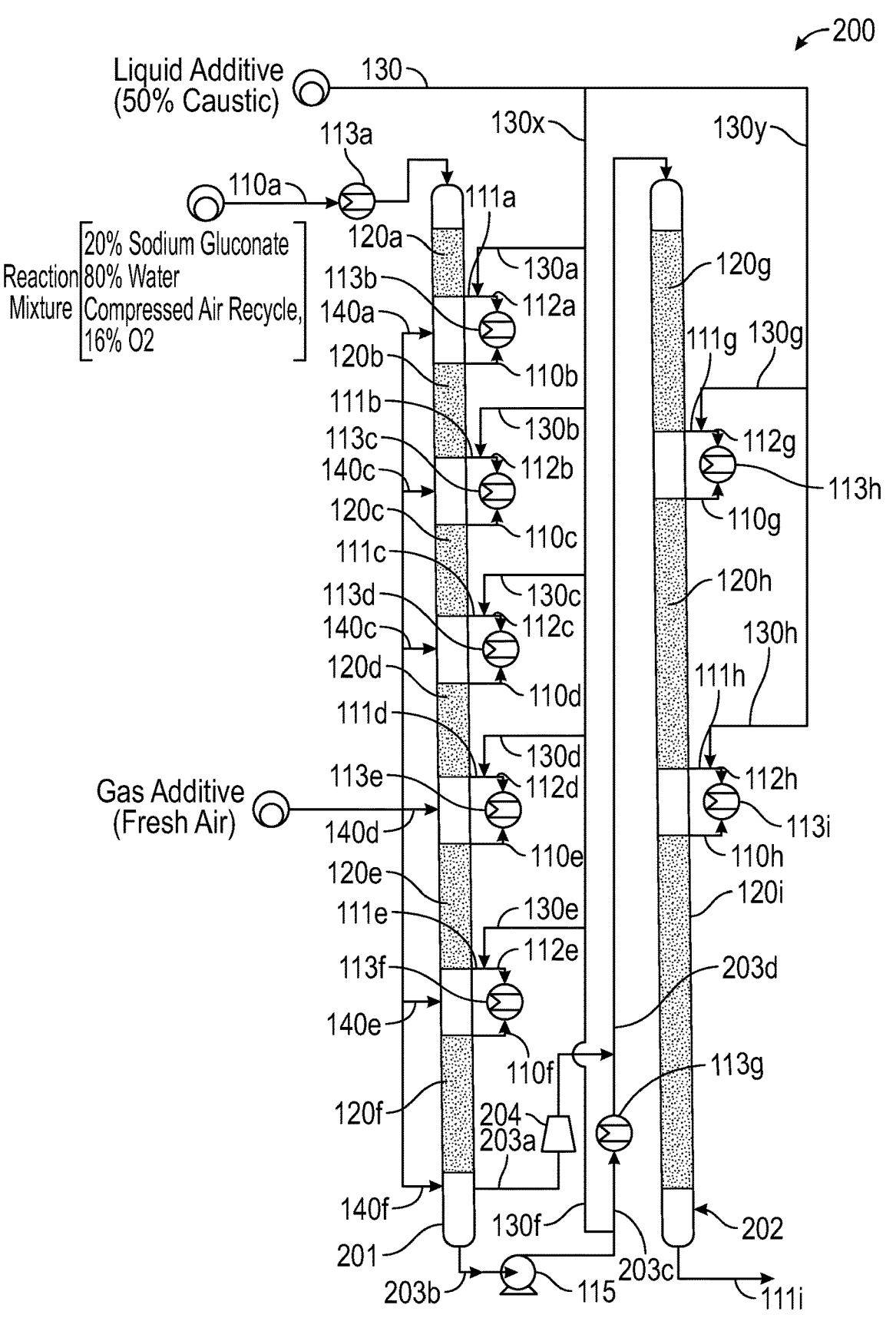
FIG. 2 is a schematic view of a reactor configuration n accordance with an aspect of the present disclosure.

FIG. 2 shows another process flow diagram of an aspect of a trickle bed apparatus 200. In FIG. 2, there are nine catalyst beds 120a-120i. Six catalyst beds 120a-f are contained in fixed bed configuration in a first vessel 201, and three catalyst beds 120g-i are contained in fixed bed configuration in a second vessel 202. The second vessel 202 is downstream of the first vessel 201 and an inlet of the second vessel 201 is fluidly connected to the outlet of the first vessel 201. While shown as having two vessels 201, 202, in general, any number of vessels can be used. Further, while shown as having nine total catalyst beds, more or less catalyst beds can be used as needed to meet one or more user and/or process objectives.

In the vessels 201 and 202, the catalyst beds can be spaced apart from one another in a vertical arrangement. In general, the spacing between the adjacent catalyst beds can be any suitable length. The gas phase can flow downward within the vessels 201 and 202 between the catalyst beds into the next catalyst bed, while liquid can be removed from each catalyst bed 120a-120h in corresponding lines 111a-h. Between each catalyst bed, the liquid can be cooled in the case of exothermic reactions or heated in the case of endothermic reactions.

In FIG. 2, gas additive can be selectively injected into the first vessel 201 via lines 140a-f at locations that are between two of the catalyst beds 120a-f. The amount of gas selectively injected via lines 140a-f can be the same in each line or selectively varied across each injection location in order to meet some user and/or process objective. During operation, the amount of gas added in these lines can be automatically controlled based on on-line process measurements. The liquid additive can be selectively injected via lines 130a-e into corresponding lines 111a-e at locations that are between catalyst beds 120a-f and corresponding heat exchangers 113b-f (e.g., upstream of the heat exchangers), for example, for an exothermic reaction. It is contemplated that liquid additive can alternatively be injected via lines 130a-e into corresponding lines 110b-f at location that are between heat exchangers 113b-f and corresponding catalyst beds 120b-f (e.g., downstream of the heat exchangers), for example, for an endothermic reaction. The amount of liquid additive selectively injected via lines 130a-e can be the same in each line or selectively varied across each injection location in order to meet some user and/or process objective. During operation, the amount of liquid added in these lines can be automatically controlled based on on-line process measurements.

In some aspects, a gas additive may not be injected into the second vessel 202. Liquid additive can be selectively injected via lines 130g-h into corresponding lines 111g-h at locations that are between catalyst beds 120g-h and corresponding heat exchangers 113h-i (e.g., upstream of the heat exchanger), for example, for an exothermic reaction. It is contemplated that liquid additive can alternatively be selectively injected via lines 130g-h into corresponding lines 110g-h at locations that are between heat exchangers 113h-i and corresponding catalyst beds 120h-i (e.g., downstream of the heat exchanger), for example, for an endothermic reaction.

FIG. 2 shows the flow of reaction mixture from the first vessel 201 to the second vessel 202 is via a gas product line 203a and a liquid/solid product line 203b. A pump 115 can be used to provide motive force to the liquid flow from the first vessel 201 to the second vessel 202. Pump 115 can be located along the liquid/solid product line 203b. Liquid additive can be injected into the liquid/solid product line 203 via line 130f to form line 203c. The combined liquid line 203c can then be heat exchanged (heated for endothermic reaction, cooled for exothermic reaction) in heat exchanger 113g. The gas product in gas product line 203a can be compressed in compressor 204, if needed, and then combined with the combined liquid line 203c to form the inlet line 203d containing gas/solid/liquid reaction mixture for introduction into the second reactor vessel 202.

When two vessels 201 and 202 are used, the liquid additive line 130 can be first split into two portions 130x and 130y. Then, portion 130x can be split into lines 130a-f for liquid injection as described above, and portion 130y can be split into lines 130g-h for liquid injection as described above.

It is contemplated that embodiments of the disclosed trickle bed reactor configurations can be used for any exothermic or endothermic chemical reaction having a large exotherm or endotherm. In an aspect, a TBR of the type disclosed herein is used to carry out liquid phase hydrogenations or liquid phase oxidations. In another aspect, a TBR of the type disclosed herein is used to carry out a series of reaction either sequentially or consecutively. For example, a TBR of the type disclosed herein may be used to carry out a dehydration reaction followed by an oxidation reaction.

In a TBR of the type disclosed herein, the gas phase may comprise air or hydrogen, and the liquid phase can be aqueous or non-aqueous. In an aspect, the solid phase, comprises catalyst particles having particle sizes ranging from about 0.4 mm to about 2 mm, alternatively from about 0.6 mm to about 1.8 mm, or alternatively from about 0.8 mm to about 1.6 mm. In an aspect, a reaction carried out in a TBR of the type disclosed herein can have an exotherm or endotherm that is greater than about 100 kJ/mol or less than about 100 kJ/mol. In some aspects, the product in a TBR reaction is an intermediate in the reaction coordinate, and gaseous and/or liquid additives are added over the course of the reaction coordinate. The rate of liquid and gas addition along the reaction coordinate can vary based on on-line process measurements such as pH or gas consumption.

An example is the exothermic catalyzed oxidation of sodium gluconate to sodium glucarate. For such a reaction, a TBR of the type disclosed herein (e.g., TBR 100 or 200) can be one or more vertically oriented vessel having catalyst beds of increasing size in a downstream direction stacked on top of one another. Operating pressures for a TBR of the type disclosed herein can range from about 50 PSI to about 100,000 PSI.

In another aspect, operating pressures for a TBR of the type disclosed herein can range from about 500 psig to about 1000 psig, alternatively from about 600 psig to about 900 psig or, alternatively from about 700 psig to about 800 psig In a further aspect, a TBR of the type disclosed herein the operating temperatures for each catalyst bed can be in the range of from about 25° C. to about 350° C., alternatively from 60° C. to about 120° C., alternatively from about 80° C. to about 110° C. or, alternatively from about 90° C. to about 100° C. In an aspect, the temperature is controlled by external heat exchangers 113a-g (for FIG. 1) or 113a-i (for FIG. 2). The feed of sodium gluconate, water, and dissolved air can be preheated in heat exchanger 113a and fed into the top of the first catalyst bed 120a.

The reactor configurations described herein offer the potential to increase the conversion and selectivity of the reactants while limiting potential byproducts. This can occur, at least in part, due to the ability to increase the productivity in the early catalyst beds where there are predominantly reactants without products, and the design reduces the productivity in the later catalyst beds where side reactions can occur between the reactants and products. It should also be appreciated that, as described herein, this result can be achieved without the need for an external cooling jacket or shell and tube design. Thus, embodiments of the configurations and designs as described herein can provide a relatively simple reactor design while improving the conversion and selectivity within the reactor itself.

In an aspect, a reactor system of the type disclosed herein is a TBR lacking a shell-and-tube design. In comparison to shell-and-tube design TBRs, the TBRs disclosed herein may offer lower operational costs. In an aspect, a TBR of the type disclosed herein allows for the facile injection of gases and/or liquids along the reactor length. In such aspects, the injected gases and/or liquids are mixed to homogeneity subsequent to injection. In an aspect, a TBR of the type disclosed herein, during reaction, is able to control the exothermic nature of the reaction without jacketing. In such aspects, control of the reaction exotherm may be achieved via external heat exchangers. In an aspect, a TBR of the type disclosed herein has a conversion rate that is increased by from about 5% to about 99% when compared to a trickle bed reactor having a core-shell configuration. In an aspect, a TBR of the type disclosed herein has a selectivity that is increased by from about 20% to about 90% when compared to a trickle bed reactor having a core-shell configuration.

7                                                                                            8

In an aspect, a TBR of the type disclosed herein is readily scalable. For example. a TBR of the type disclosed herein may have a throughput of reactant species ranging from equal to or less than about 1 kiloton per year (kta) to equal to or greater than about 100,000 kta, alternatively from about 10 kta to about 1,000 kta, or alternatively from about 100 kta to about 500 kta. The apparatus and methods disclosed herein are suitable for a three-phase reaction where the exotherm or endotherm is large. For example, the exotherm or endotherm may be equal to or less than about 100 KJ/mol, alternatively from about 10 KJ/mol to about 400 KJ/mol, alternatively from about 10 to about 200 or, alternatively from about 200 to about 400. In another aspect, the exotherm or endotherm are equal to or greater than about 100 KJ/mol, alternatively from about 10 KJ/mol to about 400 KJ/mol, alternatively from about 10 to about 200 or, alternatively from about 200 to about 400. In yet another aspect, the result of the TBR reaction is an intermediate in the reaction coordinate. In an aspect, a TBR configuration of the type disclosed herein affords the introduction of gaseous and/or liquid additives over the course of the reaction coordinate. design. For example, in order to control the operating pH, liquid additives such as acid, base, or buffer compounds can be dosed in after each reactor section, thereby controlling pH along the reaction coordinate and enhancing the overall reactivity. Gaseous additives can also be automatically added after each section, thus controlling reactivity along the reaction coordinate

Additional Disclosure

The following is provided as additional disclosure for combinations of features and aspects of the present disclosure.

A first aspect which is a trickle bed reactor, comprising a plurality of catalyst beds connected in series and progressively increasing in catalyst mass in a direction from upstream to downstream; and a plurality of heat exchangers, wherein each of the heat exchangers is located between two of the plurality of catalyst beds, and wherein each of the heat exchangers does not exchange heat with an outer surface of a vessel that contains any of the catalyst beds.

A second aspect which is the trickle bed reactor the first aspect, wherein the plurality of catalyst beds are not in a shell and tube heat exchange configuration.

A third aspect which is the trickle bed reactor of any of the first through third aspects, further comprising a gas additive line in fluid communication with at least one of the plurality of catalyst beds; or a liquid additive line in fluid communication with at least one of the plurality of catalyst beds.

A fourth aspect which is the trickle bed reactor of any of the first through third aspects, wherein productivity of the plurality of catalyst beds progressively decreases in a direction from upstream to downstream, and wherein a first productivity of the first catalyst bed is in a range of 5 to 10 times greater than a last productivity of the last catalyst bed.

A fifth aspect which is the trickle bed reactor of any of the first through fourth aspects, further comprising a first reactor vessel containing a first set of the plurality of catalyst beds; and a second reactor vessel containing a second set of the plurality of catalyst beds, wherein an inlet of the second reactor vessel is fluidly coupled to a product outlet of the first reactor vessel.

A sixth aspect which is the trickle bed reactor of the fifth aspect, wherein the product outlet of the first reactor vessel comprises a gas outlet line and a liquid outlet line, and wherein the trickle bed reactor further comprises a compressor disposed along the gas outlet line and configured to compress the gas product received from the first reactor vessel; and a pump disposed along the liquid outlet line and configured to pump the liquid product received from the second reactor vessel to the second reactor vessel, wherein the compressed gas product is configured to combine with the liquid product prior to introduction of both the liquid product and the gas product into the second reactor vessel.

A seventh aspect which is the trickle bed reactor of any of the first through sixth aspects, further comprising a feed line containing reactant and fluidly connected to the first catalyst bed of the plurality of catalyst beds, wherein the plurality of catalyst beds are configured to convert the reactants to one or more products; an effluent line containing the one or more product, wherein the effluent line is fluidly connected to the last catalyst bed of the plurality of catalyst beds.

An eighth aspect which is a method for operating a trickle bed reactor, the method comprising passing one or more reactants over a plurality of catalyst beds connected in series and progressively increasing in catalyst mass in a direction from upstream to downstream; wherein the trickle bed reactor comprises a plurality of heat exchangers, wherein each of the heat exchangers is located between two of the plurality of catalyst beds, and wherein each of the heat exchangers does not exchange heat with an outer surface of a vessel that contains any of the catalyst beds.

A ninth aspect which is the method of the eighth aspect wherein the trickle bed reactor further comprises a gas additive line in fluid communication with at least one of the plurality of catalyst beds; or a liquid additive line in fluid communication with at least one of the plurality of catalyst beds.

A tenth aspect which is the method of any of the eighth through ninth aspects, wherein the reactants comprise sodium gluconate and the catalyst beds comprise an oxidation catalyst.

An eleventh aspect which is the method of the tenth aspect. wherein at least a portion of the reactants form an oxidized product.

A twelfth aspect which is the method of the eleventh aspect, wherein the oxidized products comprise sodium glucarate.

A thirteenth aspect which is the method of any of the eighth through twelfth aspects, further comprising introducing additional sodium gluconate to the trickle bed reactor via the liquid additive line.

A fourteenth aspect which is the method of any of the eighth through thirteenth aspects, wherein the trickle bed reactor lacks a core-shell configuration.

A fifteenth aspect which is the method of any of the eighth through fourteenth aspects, wherein the catalyst mass increases by from about 100 kg to about 1,000,000 kg.

A sixteenth aspect which is the method of any of the eighth through fifteenth aspects, wherein the operating pressures for the trickle bed reactor ranges from about 50 PSI to about 100,000 PSI.

A seventeenth aspect which is the method of any of the eighth through sixteenth aspects, wherein the operating temperatures for the trickle bed reactor ranges from about 25° C. to about 350° C.

An eighteenth aspect which is the method of any of the eighth through seventeenth aspects wherein the trickle bed reactor has a conversion rate that is increased by from about 5% to about 99% when compared to a trickle bed reactor having a core-shell configuration.

A nineteenth aspect which is the method of any of the eighth through eighteenth aspects wherein the trickle bed reactor has a selectivity that is increased by from about 20% to about 90% when compared to a trickle bed reactor having a core-shell configuration.

A twentieth aspect which is the method of any of the eighth through nineteenth aspects wherein the trickle bed reactor has an output of from equal to or less than about 1 kiloton per year to equal to or greater than about 100,000 kiloton per year.

EXAMPLES

The presently disclosed subject matter having been generally described, the following examples are given as particular aspects of the subject matter and to demonstrate the practice and advantages thereof. It is understood that the examples are given by way of illustration and are not intended to limit the specification or the claims in any manner.

Kinetic models were made for the liquid phase oxidation of sodium gluconate, calcium gluconate, glucoheptonate, sucrose, maltose, fructose, glucuronic acid, guluronic acid, glucose, glucodialdose, and other similar organic compounds using air and water over a core-shell Au/C extrudate catalyst to demonstrate the advantages of the disclosed trickle bed reactor configurations. The initial reaction mixture contained a liquid phase composition of 20 wt % organic compound and 80 wt % water mixed with gas phase of compressed air (16 vol % $O_2$). This reaction has a high exotherm (ca. 500 kJ/mol) and requires the interstage injection of liquid caustic (NaOH) for the reaction to proceed along the desired reaction coordinate. The rate of caustic addition can be a set amount or be automatically controlled by pH of the process fluid depending on the desired reaction scheme. An amount of 50 g of Au/C catalyst (0.3 wt % on 1.5×3 mm carbon extrudate trilobes) was loaded into a catalyst bed of a downflow trickle bed reactor of ¾" O.D. tubing. Glass spheres having a diameter of ~200 µm were used to fill the void space between the extrudates in the inner wall of the reactor. The metal oxidation of these organic compounds was performed under different reactant concentrations, flowrates, conversions, $O_2$:organic compound feed ratios, $O_2$:$N_2$ ratios, temperatures, pressures, and excess caustic concentrations to build the kinetic model. An equation of state for dissolved oxygen concentration was used from Desmond Tromans, *Hydrometallurgy* 48 (1998) 327-342.

The total catalyst loading in each of the following examples was equal, for comparison of the inventive trickle bed reactor configuration disclosed herein to an ideal trickle bed reactor and to a trickle bed reactor configuration that has the same mass of catalyst in each catalyst bed.

Example 1

Example 1 is kinetic modeling for an ideal isothermal fixed bed, PFR apparatus where caustic and fresh air was injected continuously at each infinitesimal point along the reaction coordinate. While such an ideal PFR cannot be constructed in reality, it is informative for comparison to the inventive trickle bed configurations disclosed herein. The design equation used for the kinetic model of the ideal isothermal PFR was:

$$\frac{dX}{dW} = \frac{-r_{GO}}{F_{GO}} \qquad \text{Equation 1}$$

where dX is the differential conversion, dW is the differential catalyst weight, $r_{GO}$ is the reaction rate with respect to liquid feedstock consumption, and $F_{GO}$ is the flow rate of liquid feedstock.

Example 2

Example 2 is kinetic modeling for five catalyst beds having total catalyst loading equivalent to the catalyst loading in Example 1, the five catalyst beds being connected in series with cooling of the reaction mixture between catalyst beds. The design equations used for the kinetic model of this comparative trickle bed reactor was:

$$\frac{dX}{dW} = \frac{-r_{GO}}{F_{GO}} \qquad \text{Equation 1}$$

$$\frac{dT}{dW} = \frac{-r_{GO}\Delta H_{rxn}}{C_p \dot{m}_{tot}} \qquad \text{Equation 2}$$

$$\frac{dP}{dW} = -dP - \frac{F_{O_2}}{F_{O_2} + F_{N_2}} \qquad \text{Equation 3}$$

where for Equation 1: dX is the differential conversion, dW is the differential catalyst weight, $r_{GO}$ is the reaction rate with respect to organic feedstock consumption, and $F_{GO}$ is the flow rate of organic feedstock; for Equation 2: dT is differential temperature, dW is the differential catalyst weight, $-r_{GO}$ is the reaction rate with respect to liquid feedstock consumption, $\Delta H_{rxn}$ is the heat of reaction in units of kJ/mol, $C_p$ is heat capacity in units of kJ/mol/K, and $\dot{m}_{tot}$ is total mass flow rate through the system; and for Equation 3: dP is the differential pressure, dW is the differential catalyst weight, $-dP$ is the frictional pressure drop, $F_{O2}$ is the flow rate of oxygen, and $F_{N2}$ is the flow rate of nitrogen.

Example 3

Example 3 involved kinetic modeling of nine catalyst beds connected in series with cooling of the reaction mixture between catalyst beds in a configuration similar to that shown in the apparatus 100 of FIG. 1, except there are nine catalyst beds in Example 3 instead of the seven catalyst beds shown in FIG. 1. The beds of Example 3 had successively larger masses of catalyst from an upstream to a downstream direction, similar to the pattern shown for catalyst beds 120*a-g* in FIG. 1. The total catalyst loading in Example 3 was equivalent to the catalyst loading in Example 1 and in Example 2. The design equations used for the kinetic model of the inventive trickle bed reactor was:

$$\frac{dX}{dW} = \frac{-r_{GO}}{F_{GO}} \qquad \text{Equation 1}$$

$$\frac{dT}{dW} = \frac{-r_{GO}\Delta H_{rxn}}{C_p \dot{m}_{tot}} \qquad \text{Equation 2}$$

$$\frac{dP}{dW} = -dP - \frac{F_{O_2}}{F_{O_2} + F_{N_2}} \qquad \text{Equation 3}$$

where for Equation 1: dX is the differential conversion, dW is the differential catalyst weight, $r_{GO}$ is the reaction rate with respect to gluconate consumption, and $F_{GO}$ is the flow rate of gluconate; for Equation 2: dT is the differential temperature, dW is the differential catalyst weight, $-r_{GO}$ is the reaction rate with respect to gluconate consumption,

US 12,583,810 B2

11

$\Delta H_{rxn}$ is the heat of reaction in units of kJ/mol, $C_p$ is heat capacity in units of kJ/mol/K, and $\dot{m}_{tot}$ is total mass flow rate through the system; and for Equation 3: dP is the differential pressure, dW is the differential catalyst weight, −dP is the frictional pressure drop, $F_{O2}$ is the flow rate of oxygen, and $F_{N2}$ is the flow rate of nitrogen.

Figure 3:
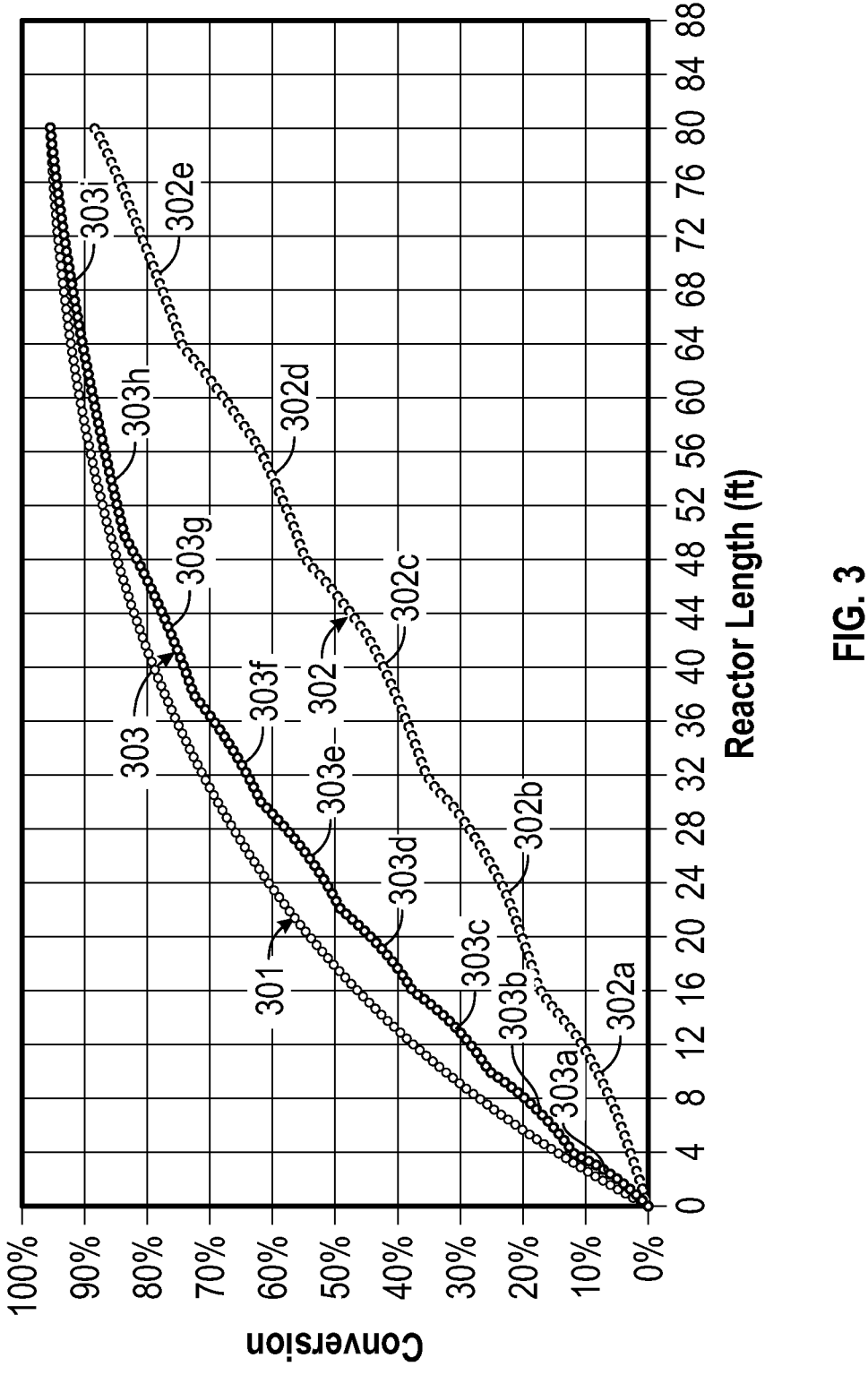
FIG. 3 is a graph illustrating the reactor length versus conversion for the kinetic modeling performed in Examples 1 to 3.

FIG. 3 illustrates a graph of reactor length versus conversion for the kinetic modeling performed in Examples 1 to 3. Curve 301 is the ideal isothermal PFR from Example 1, curve 302 is the five equally-sized catalyst bed trickle bed reactor of Example 2, and curve 303 is the nine catalyst bed trickle bed reactor of Example 3.

The curve 301 for the ideal isothermal PFR is impossible to achieve, and is an ideal scenario. However, the ideal scenario is useful for comparison to the traditional trickle bed reactor configuration in Example 2 and the inventive trickle bed reactor configuration in Example 3.

Curve 302 contains five smaller curves 302a-e, one curve for each of the five equally-sized catalyst beds in the traditional trickle bed reactor of Example 2. The low conversion in curves 302a-b is because the catalyst beds of the first two reactors are too big to manage the reaction exotherm. As such, the first two catalyst beds must be operated at a lower temperature than ideal so that the progressive exotherm does not lead to thermal runaway. That is, in exchange for being able to operate the five equally-sized catalyst beds without runaway reaction in the upstream catalyst beds, conversion is sacrificed by having to operate those beds at lower temperatures. The gap between curve 302 and the ideal curve 301 illustrates the difference between the conversion actually achieved when using trickle bed reactors of equal catalyst loading versus the ideal scenario.

Curve 303 contains nine smaller curves 303a-i, one curve for each of the nine catalyst beds in the inventive trickle bed reactor configuration of Example 3. Curves 303a-i show the smaller catalyst beds in the beginning of the reactor (e.g., curves 303a-f) have a higher conversion than the traditional trickle bed reactor configuration of curve 302. The upstream catalyst beds were able to operate at higher temperatures while still controlling the reaction exotherm. The higher operating temperatures gave a higher conversion in the upstream catalyst beds, and the conversion approaches the ideal isothermal PFR in curve 301. The gap between curve 303 and the ideal curve 301 illustrates the difference between the conversion actually achieved when using the inventive trickle bed configuration disclosed herein is more like the ideal scenario than the traditional trickle bed reactor configuration. Considering that ideal operation is desired, the conversion achieved by the inventive catalyst bed configuration is an improvement over the traditional catalyst bed configuration.

Figure 4:
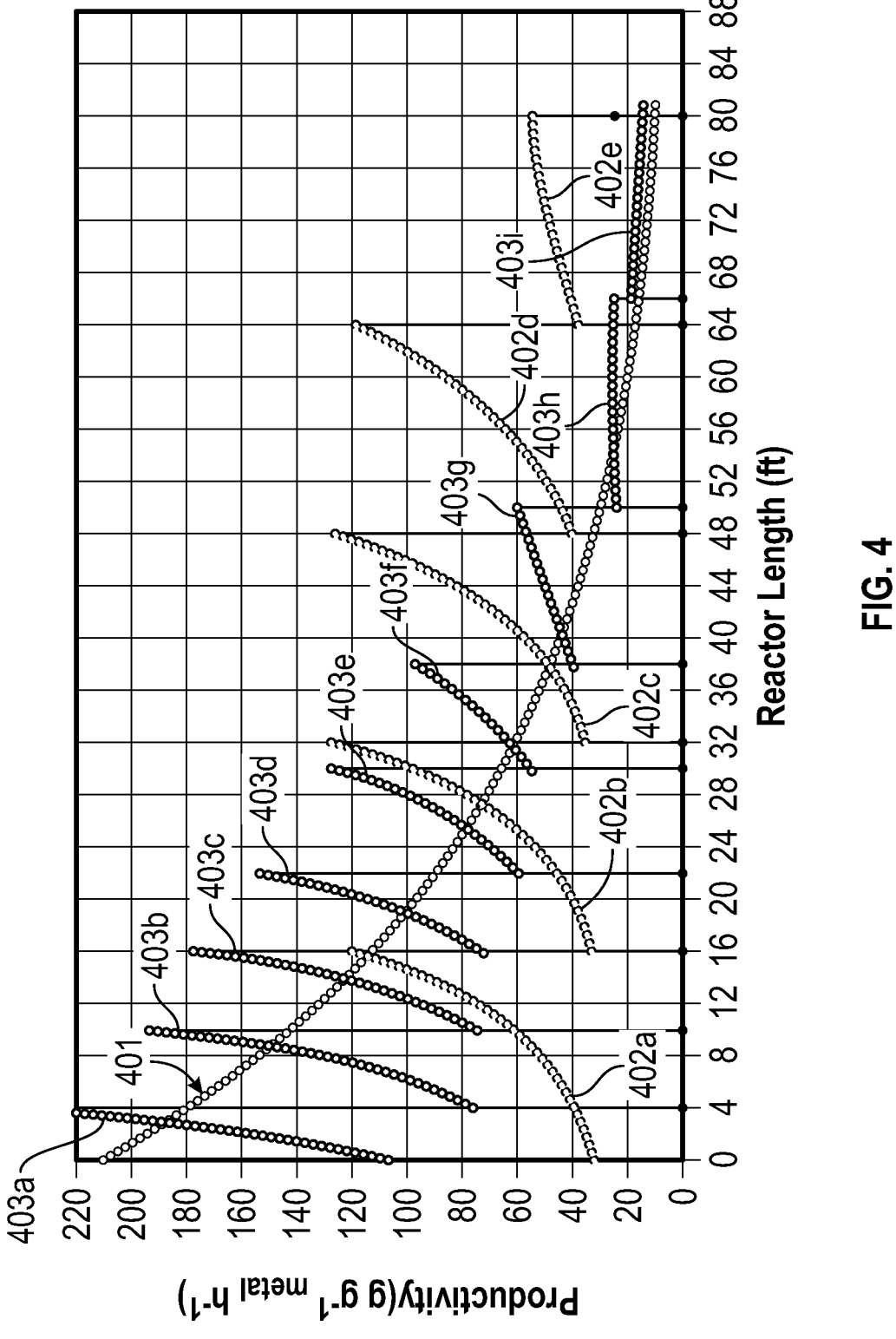
FIG. 4 is a graph illustrating the reactor length versus productivity for the kinetic modeling performed in Examples 1 to 3.

FIG. 4 illustrates a graph of reactor length versus productivity for the kinetic modeling performed in Examples 1 to 3. Curve 401 is the ideal isothermal PFR from Example 1, curves 402a-e are the curves for each of the five equally-sized catalyst beds in the traditional trickle bed reactor of Example 2, and curves 403a-i are the curves for each of the nine catalyst beds in the inventive trickle bed reactor of Example 3.

The curve 401 for the ideal isothermal PFR is impossible to achieve, and is an ideal scenario. However, the ideal scenario is useful for comparison to the traditional trickle bed reactor configuration in Example 2 and the inventive trickle bed reactor configuration in Example 3.

Curves 402a-e show the productivity for each of the five equally-sized catalyst beds in the traditional trickle bed reactor of Example 2. The low productivity in curves 402a-b is because the catalyst beds of the first two reactors are too big to manage the reaction exotherm. As such, the first two catalyst beds must be operated at a lower temperature than ideal so that the progressive exotherm does not lead to thermal runaway. That is, in exchange for being able to operate the five equally-sized catalyst beds without runaway reaction in the upstream catalyst beds, productivity is sacrificed by having to operate at lower temperatures. The gap between curves 402a-e and the ideal curve 401 illustrates the difference between the productivity actually achieved when using trickle bed reactors of equal catalyst loading versus the ideal scenario. The periodic drops in productivity to 0 $g_{converted}\,g^{-1}_{metal}\,h^{-1}$ correspond to the interstage coolers.

Curves 403a-i show the productivity for each of the nine catalyst beds in the inventive trickle bed reactor configuration of Example 3. Curves 403a-i show the smaller catalyst beds in the beginning of the reactor (e.g., curves 403a-e) have a higher productivity than the traditional trickle bed reactor configuration of curves 402a-b. The upstream catalyst beds were able to operate at higher temperatures while still controlling the reaction exotherm. The higher operating temperatures gave a higher productivity in the upstream catalyst beds, and the productivity crosses the productivity of the ideal isothermal PFR in curve 401. The higher productivity of the traditional catalyst beds in curves 402c-e does not make up for the lower productivity in the initial catalyst beds in curves 402a-b. This is because the higher productivity for the downstream catalyst beds in Example 2, shown by curves 402c-e, generates more unwanted reaction byproducts and thus the productivity in the downstream catalyst beds is wasted on generation of non-desired products. In contrast, productivity is highest in the upstream catalyst beds of Example 3 as shown in curves 403a-f, and later in the reaction coordinate, the productivity of the downstream catalyst beds shown by curves 403g-i is lower, resulting in a lower amount of unwanted byproducts generated in the inventive configuration. The periodic drops in productivity to 0 $g_{converted}\,g^{-1}_{metal}\,h^{-1}$ correspond to the interstage coolers.

While aspects of the presently disclosed subject matter have been shown and described, modifications thereof can be made by one skilled in the art without departing from the spirit and teachings of the subject matter. The aspects described herein are exemplary only and are not intended to be limiting. Many variations and modifications of the subject matter disclosed herein are possible and are within the scope of the disclosed subject matter. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an aspect of the present disclosure. Thus, the claims are a further description and are an addition to the aspects of the present invention. The discussion of a reference herein is not an admission that it is prior art to the presently disclosed subject matter, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A trickle bed reactor, comprising:
a plurality of catalyst beds connected in series and progressively increasing in catalyst mass in a direction from upstream to downstream; and
a plurality of heat exchangers, wherein each of the heat exchangers is located between two of the plurality of catalyst beds, wherein each heat exchanger of the plurality of heat exchangers is configured to adjust a temperature of a reaction mixture passing through the heat exchanger to initiate a reaction in a subsequent catalyst bed of the plurality of catalyst beds, and wherein each of the heat exchangers is an external heat exchanger that does not exchange heat with an outer surface of a vessel that contains any of the catalyst beds.

2. The trickle bed reactor claim 1, wherein the plurality of catalyst beds are not in a shell-and-tube heat exchange configuration.

3. The trickle bed reactor of claim 1, further comprising:
a gas additive line in fluid communication with at least one of the plurality of catalyst beds via a line at a location between one of the plurality of heat exchangers and one of the plurality of catalyst beds; and
a liquid additive line in fluid communication with at least one of the plurality of catalyst beds via a line at a location between one of the plurality of heat exchangers and one of the plurality of catalyst beds.

4. The trickle bed reactor of claim 1, wherein productivity of the plurality of catalyst beds progressively decreases in a direction from upstream to downstream, and wherein a first productivity of the first catalyst bed is in a range of 5 to 10 times greater than a last productivity of the last catalyst bed.

5. The trickle bed reactor of claim 1, further comprising:
a first reactor vessel containing a first set of the plurality of catalyst beds; and
a second reactor vessel containing a second set of the plurality of catalyst beds, wherein an inlet of the second reactor vessel is fluidly coupled to a product outlet of the first reactor vessel.

6. The trickle bed reactor of claim 5, wherein the product outlet of the first reactor vessel comprises a gas outlet line and a liquid outlet line, and wherein the trickle bed reactor further comprises:
a compressor disposed along the gas outlet line and configured to compress the gas product received from the first reactor vessel; and
a pump disposed along the liquid outlet line and configured to pump the liquid product received from the first reactor vessel to the second reactor vessel,
wherein the compressed gas product is configured to combine with the liquid product prior to introduction of both the liquid product and the gas product into the second reactor vessel.

7. The trickle bed reactor claim 1, further comprising:
a feed line containing reactant and fluidly connected to the first catalyst bed of the plurality of catalyst beds, wherein the plurality of catalyst beds are configured to convert the reactants to one or more products;
an effluent line containing the one or more product, wherein the effluent line is fluidly connected to the last catalyst bed of the plurality of catalyst beds.

8. A method for operating a trickle bed reactor, the method comprising: passing one or more reactants over a plurality of catalyst beds connected in series and progressively increasing in catalyst mass in a direction from upstream to downstream;
wherein the trickle bed reactor comprises a plurality of heat exchangers, wherein each of the heat exchangers is located between two of the plurality of catalyst beds, and wherein each of the heat exchangers is an external heat exchanger that does not exchange heat with an outer surface of a vessel that contains any of the catalyst beds;
converting the one or more reactants to one or more products over the plurality of catalyst beds to form a reaction mixture;
adjusting a temperature of the reaction mixture to a temperature configured to initiate a reaction in a subsequent catalyst bed of the plurality of catalyst beds; and
passing the reaction mixture having the adjusted temperature to the subsequent catalyst bed.

9. The method of claim 8, wherein the trickle bed reactor further comprises: a gas additive line in fluid communication with at least one of the plurality of catalyst beds via a line at a location between one of the plurality of heat exchangers and one of the plurality of catalyst beds; and
a liquid additive line in fluid communication with at least one of the plurality of catalyst beds via a line at a location between one of the plurality of heat exchangers and one of the plurality of catalyst beds.

10. The method of claim 8, wherein the reactants comprise sodium gluconate and the catalyst beds comprise an oxidation catalyst.

11. The method of claim 10, wherein at least a portion of the reactants form an oxidized product.

12. The method of claim 11, wherein the oxidized products comprise sodium glucarate.

13. The method of claim 9, further comprising introducing additional sodium gluconate to the trickle bed reactor via the liquid additive line.

14. The method of claim 8, wherein the trickle bed reactor lacks a shell-and-tube configuration.

15. The method of claim 8, wherein the catalyst mass increases by from about 100 kg to about 1,000,000 kg.

16. The method of claim 8, wherein an operating pressure for the trickle bed reactor ranges from about 50 PSI to about 100,000 PSI.

17. The method of claim 8, wherein an operating temperature for the trickle bed reactor ranges from about 25° C. to about 350° C.

18. The method of claim 8, wherein the trickle bed reactor has a conversion rate that is increased by from about 5% to about 99% when compared to a trickle bed reactor having a shell-and-tube configuration.

19. The method of claim 8, wherein the trickle bed reactor has a selectivity that is increased by from about 20% to about 90% when compared to a trickle bed reactor having a shell-and-tube configuration.

20. The method of claim 8, wherein the trickle bed reactor has an output of from equal to or greater than about 1 kiloton per year to equal to or less than about 100,000 kiloton per year.

* * * * *